United States Patent [19]
Frijlink

[11] Patent Number: 5,457,727
[45] Date of Patent: Oct. 10, 1995

[54] DEVICE FOR PROCESSING A MEASURED SIGNAL CORRESPONDING TO THE INTENSITY OF X-RAYS REFLECTED BY A MULTI-LAYER STRUCTURE ON A SUBSTRATE

[75] Inventor: Peter Frijlink, Crosne, France

[73] Assignee: U.S. Philips Corporation, New York, N.Y.

[21] Appl. No.: 79,300

[22] Filed: Jun. 17, 1993

[30] Foreign Application Priority Data

Jun. 17, 1992 [FR] France .................................. 9207350

[51] Int. Cl.⁶ .............................................. G01N 23/207
[52] U.S. Cl. ............................................. 378/73; 378/71
[58] Field of Search ................................. 378/70, 71, 73, 378/76, 77, 84

[56] References Cited

U.S. PATENT DOCUMENTS 4,785,470  11/1988  Wood et al. ................................ 378/84
5,003,569  3/1991   Okada et al. .............................. 378/70

FOREIGN PATENT DOCUMENTS 0468582  7/1991  European Pat. Off. ........ G01N 23/20
1389435  4/1990  U.S.S.R. .................................... 378/76

Primary Examiner—David P. Porta
Assistant Examiner—David Vernon Bruce
Attorney, Agent, or Firm—Jack D. Slobod

[57] ABSTRACT

A device for processing a measured signal corresponding to the intensity reflected, as a function of the glancing angle ($\theta$) at an X-ray wavelength ($\lambda_{RX}$), by a real multi-layer structure stacked on a substrate (100), which layers exhibit small differences as regards refractive index at their interfaces, transforms the function (f($\theta$)), corresponding to the reflected intensity signal measured as a function of the glancing angle ($\theta$) in a range of glancing angles which is bounded by minimum and maximum angular values $\theta_{min}$–$\theta_{max}$, into a function (F(d)) corresponding to the intensity signal formulated as a function of the depth (d) within the real multi-layer structure, the function (F(d)) obtained enabling a direct representation to be formed of the depth of each interface ($d_1, d_2, \ldots d_n$) of the real structure, and of the associated reflected intensities.

14 Claims, 8 Drawing Sheets

DEVICE FOR PROCESSING A MEASURED SIGNAL CORRESPONDING TO THE INTENSITY OF X-RAYS REFLECTED BY A MULTI-LAYER STRUCTURE ON A SUBSTRATE

FIELD OF THE INVENTION

The invention relates to a device for processing a measured signal corresponding to the intensity reflected, as a function of the glancing angle ($\theta$) at an X-ray wavelength ($\lambda_{RX}$), by a real multi-layer structure stacked on a substrate, which layers exhibit small differences as regards refractive index at their interfaces.

A glancing angle is to be understood to mean herein the angle enclosed by the incident beam relative to the reflective surface, i.e. the angle which is the complement of the angle of incidence.

The invention can be used for the implementation of a device for testing multi-layer structures; for example, it can be used for automatically determining the thickness and the nature or composition of periodic multi-layer mirror layers, or stacked heterostructures of semiconductor materials.

BACKGROUND OF THE INVENTION

From prior art (EP 0 468 582) there is already known an X-ray diffractometer apparatus comprising optical means for measuring the reflectivity of a solid specimen. This apparatus is used for determining structural parameters of multilayer mirrors operating in the X-ray domain and formed by two-layer stacks of materials having a high and a low refractive index. This apparatus enables comparison of the parameters calculated on the basis of the reflectivity curve and the parameters known from classification tables.

The cited document discloses a control system for selecting the appropriate optical filters from filters having different absorption coefficients and for triggering their introduction into the path of the X-ray beam reflected by a structure to be tested. Thanks to this system, the reflected intensity can be measured by means of a proportional counter in such a manner that the latter never leaves its linear operating range, regardless of the intensity values. A proportional counter is to be understood to mean herein a device which contains gases which can be ionized by the photon flux to be detected, and which supplies a signal in the form of a voltage which is proportional to the number of photons received.

The known apparatus comprises a system for applying the output signal of the proportional counter to a device for processing this signal in which a computer program enables interlinking of the various parts of the reflectivity curve obtained in a relation with each of the filters of the controlled system. A smooth reflectivity curve is thus obtained.

This reflectivity curve, established at a constant wavelength $\lambda_{RX}$ of an X-ray source X and as a function of the variations of the glancing angle $\theta$, decreases strongly between the so-called critical value $\theta_c$, at which the reflectivity equals 1, and values where the glancing angle is still small, i.e. smaller than or approximately equal to 4° (degrees). Therefore, a controlled system of filters is used so that all intensity measurements can be carried out without departing from the linear range of the proportional counter. This curve also exhibits a given number of marked maxima of the reflected intensity which appear for specific glancing angles. The values of the glancing angles $\theta$ corresponding to the maxima satisfy Bragg's law:

$2d \sin \theta = k\lambda$ (where k=constant=an integer), and enable calculation of the period D of the layers of a periodic multi-layer system.

This determination, however, corresponding to the orders of the reflection, should also take into account the nature of the materials of the layers. Therefore, according to the teaching of the cited document, the pitch D of the periodic layers of multi-layer mirrors is determined, on the basis of the smoothed reflectivity curve, by comparison with theoretical curves constructed on the basis of classification tables.

Nevertheless, the device can be used only in cases where the reflectivity curve exhibits maxima which can be distinguished, i.e. sufficiently marked maxima, to enable exact measurement of their position in respect of glancing angle value. This method is thus restricted to the multi-layer structures formed by periodic stacks of layers whose material compositions are known and whose refractive indices deviate substantially, as well as to the multi-layer mirrors of known structure which do not have a large thickness and in which the period is not too small.

SUMMARY OF THE INVENTION

Therefore, it is an object of the invention to provide a device for automatically determining the thickness and the composition of layers of multi-layer structures in the particularly difficult cases where:

the layer thicknesses are not periodic but differ throughout the structure;

the materials of the structure are not recurrent in a periodic manner;

moreover, the refractive indices of the materials approximate one another very closely from one layer to another;

and, moreover, given layers may be extremely thin, for example less than 1 nm.

This object is achieved by means of a device as defined in the preamble and having the characteristics disclosed in claim 1.

BRIEF DESCRIPTION OF THE DRAWINGS

The invention will be described in detail hereinafter with reference to the accompanying drawings; therein:

FIG. 1b shows the reflected intensity $f(\theta)$ as a function of the glancing angle $\theta$ for the structure shown in FIG. 1a;

DESCRIPTION OF EMBODIMENTS

Figure 1A:
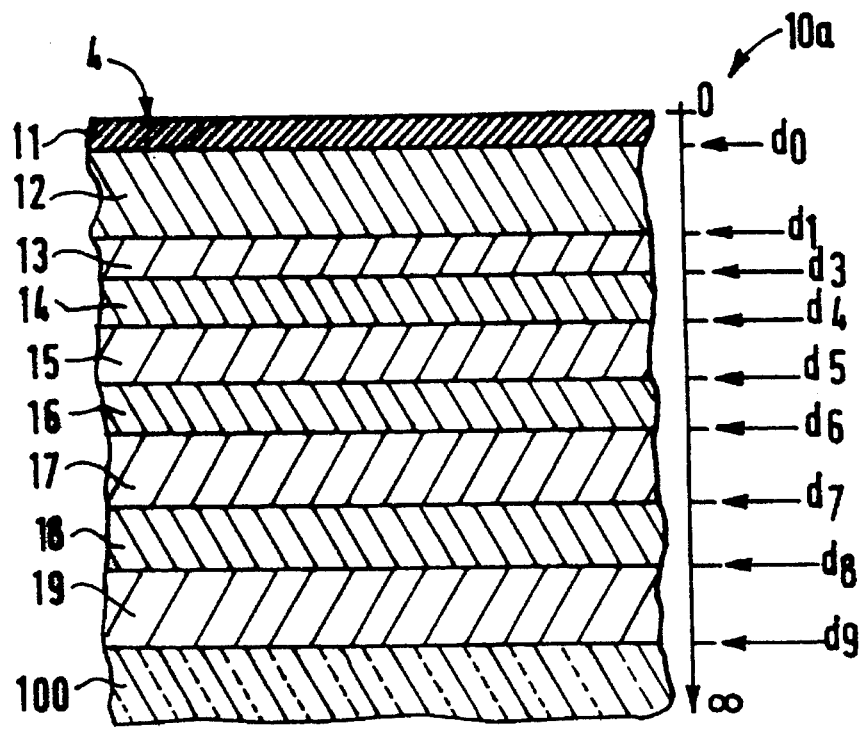
FIG. 1a shows a layer structure formed on a substrate and tested by means of the device in accordance with the invention.
Figure 4:
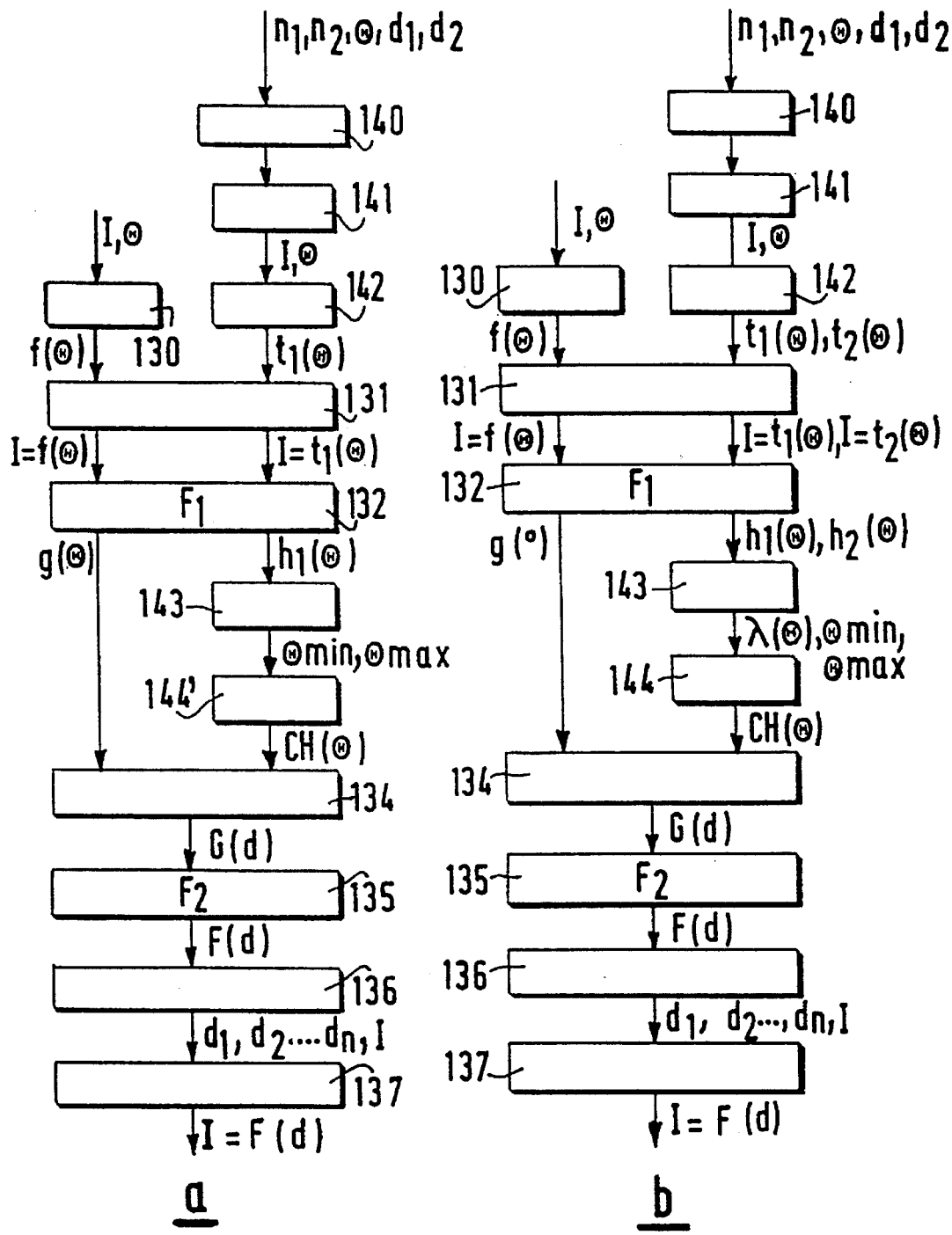
FIG. 4a shows a simplified flow chart used in accordance with the invention.
FIG. 4b shows a flow chart for a more exact implementation.

Referring to the FIG. 1a and the FIGS. 4a, b, the invention proposes to provide a device for processing a measured signal corresponding to the intensity I reflected, at an X-ray wave-length $\lambda_{RX}$, by a real multi-layer structure stacked on a substrate 100, which layers exhibit small differences in respect of refractive index at their interfaces, said processing device comprising means for performing the transformation of the function f(θ), corresponding to the reflected intensity signal measured as a function of the glancing angle θ in a range of glancing angles which is limited by the minimum and maximum angle values $\theta_{min}$ and $\theta_{max}$, respectively, into a function F(d) corresponding to the intensity signal formulated as a function of the depth d in the real multi-layer structure, said function F(d) obtained enabling a diagram to be drafted directly of the depth of each interface $d_1, d_2, \ldots d_n$ of the real structure and the associated reflected intensities.

The range $\theta_{min}-\theta_{max}$ will be defined hereinafter.

Figure 7:
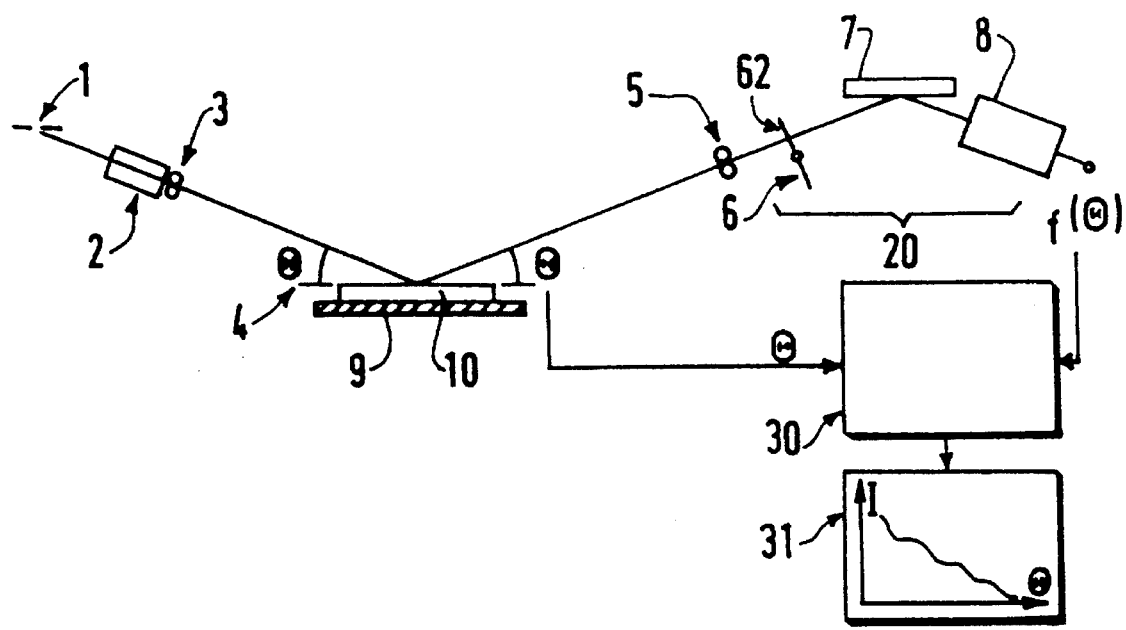
FIG. 7 shows an X-ray diffractometer.

Referring to FIG. 7, those skilled in the art can utilize an X-ray diffractometer in order to measure the intensity reflected by a specimen to be tested as a function of the glancing angle θ.

The known apparatus, for example the type number PW1050 marketed by Philips, comprises at least:

a source system 1, 2, 3 comprising:

a linear X-ray source 1;

a collimator system 2 and 3, including Soller slits 2 and a diverging slit 3;

a goniometer specimen support 9, comprising means (not shown) for orienting a specimen 10; these means comprise notably a system for selecting and storing the value of the glancing angle θ enclosed by the beam from the source system 1, 2, 3 relative to the upper plane 4 of the specimen 10;

and a system 20 for capturing the reflected flux, comprising:

a collimator system 5 which is formed by a so-called receiving slit;

a monochromator 7 for the X-ray range, for example a graphite monochromator;

a detector 8 for the X-ray flux, for example a proportional counter;

and possibly a filter system 62 which is arranged in a filter support 6.

However, any apparatus capable of measuring the intensity I=f(θ) of a glancing beam of X-rays reflected by a specimen to be tested, as a function of the glancing angle θ, can be used instead of the apparatus described above.

When the apparatus according to FIG. 7 is used, the proportional counter 8 supplies a signal which is proportional to the flux of photons received and which is applied, with the value of the angles θ corresponding to each value proportional to the intensity I, to a means 30 for storing this data. The known device possibly comprises a curve plotter 31 which is capable of plotting, on the basis of data supplied by the storage means 30, a continuous curve which represents the intensity f(θ), in the ordinate in arbitrary units (UA) between 0 and 1, as a function of the glancing angle θ, plotted in degrees on the abscissa.

Referring to FIG. 1a, a multi-layer structure 10a is to be tested by means of the device in accordance with the invention. The structure 10a comprises, starting from its upper surface 4:

an oxide layer 11;

layers 12, 14, 16, 18 of gallium arsenide semiconductor material (GaAs);

layers 13, 15, 17, 19 of another gallium arsenide and aluminium semiconductor material $(Ga_xAl_{1-x}As)$ which form heterostructures with the alternating GaAs layers;

a gallium arsenide (GaAs) substrate 100;

In this test specimen:

the distances $d_1, d_2, d_3, \ldots d_n$ between the upper surface 4 and each of the GaAs/GaAlAs interfaces are unknown, because the exact thickness of each of the layers, formed by epitaxial growth, is unknown;

the exact composition of the GaAlAs layers is unknown, i.e. the concentration x is unknown;

the refractive index of the material GaAlAs is very close to that of GaAs.

Figure 1B:
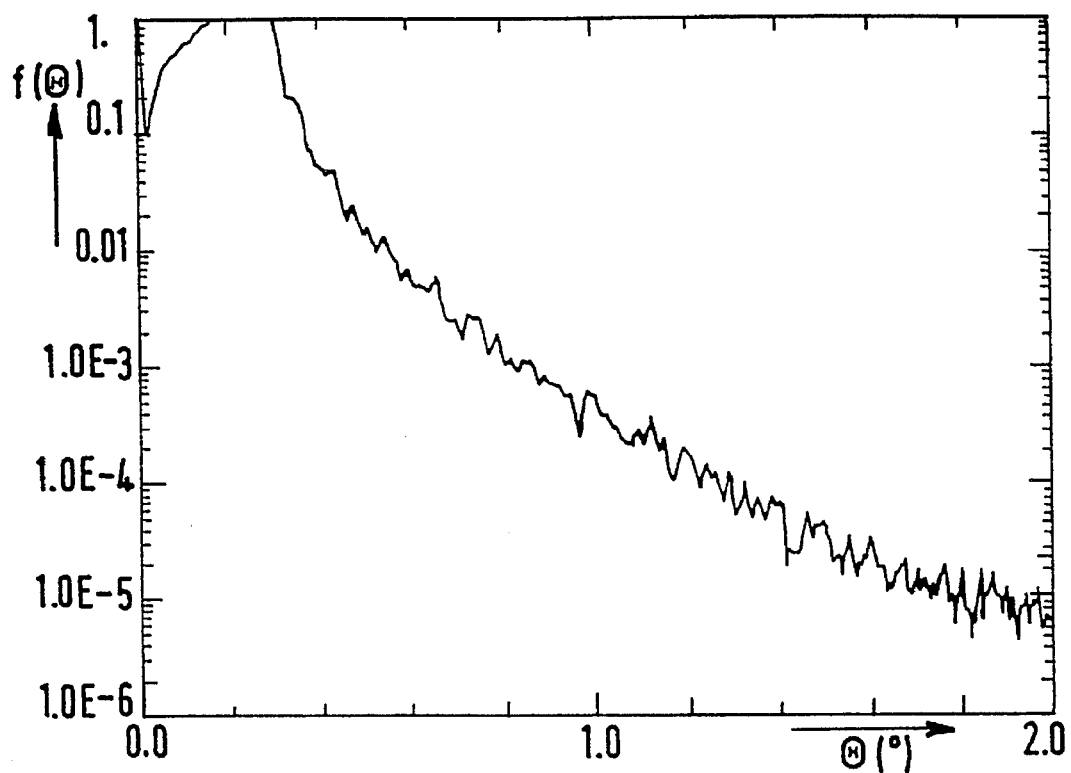

FIG. 1b shows the experimental curve of the reflectivity of the specimen 10a to be tested, representing the measured values f(θ) of the reflected intensity I of the X-rays as a function of the glancing angle θ.

It has already been stated that in the diffractometer shown in FIG. 7 the X-ray source emits a beam of rays incident at an angle θ relative to the surface 4 of the specimen 10 to be tested, said rays being reflected at the same angle θ by the various surfaces and interfaces of the specimen. Each of the interfaces, starting with the interface between air and the first layer of material, causes reflections. The rays thus reflected interfere optically and are constructive for given values of the glancing angle θ and destructive for other values. It appears that in the case where the first interface is that between air and the semiconductor layer, the first reflection is of an intensity which is much higher than that of the other reflections. Consequently, this interference effect, be it constructive or destructive, causes overmodulation which is superposed on a generally descending curve of the intensity I as a function of θ as shown in FIG. 1b. If the structure were to consist of a single interface between air and material, the reflectivity curve would only be a descending and smooth type. The overmodulation is a characteristic effect of multi-layer structures.

It appears that on the basis of this direct measurement of the intensity reflected by a multi-layer specimen, it is absolutely impossible to perform the measurement producing the position $d_1, d_2, \ldots d_n$ of the interfaces with respect to the upper surface of the specimen, or the measurement of the thickness of a layer in the multi-layer structure.

It is an object of the invention to provide a device for directly determining the positions $d_1$, $d_2$, $d_3$ ... $d_n$ of the interfaces with respect to the upper surface of the specimen on the basis of the reflected intensity $I=f(\theta)$ of the X-ray beam, measured as a function of $\theta$.

Figure 6:
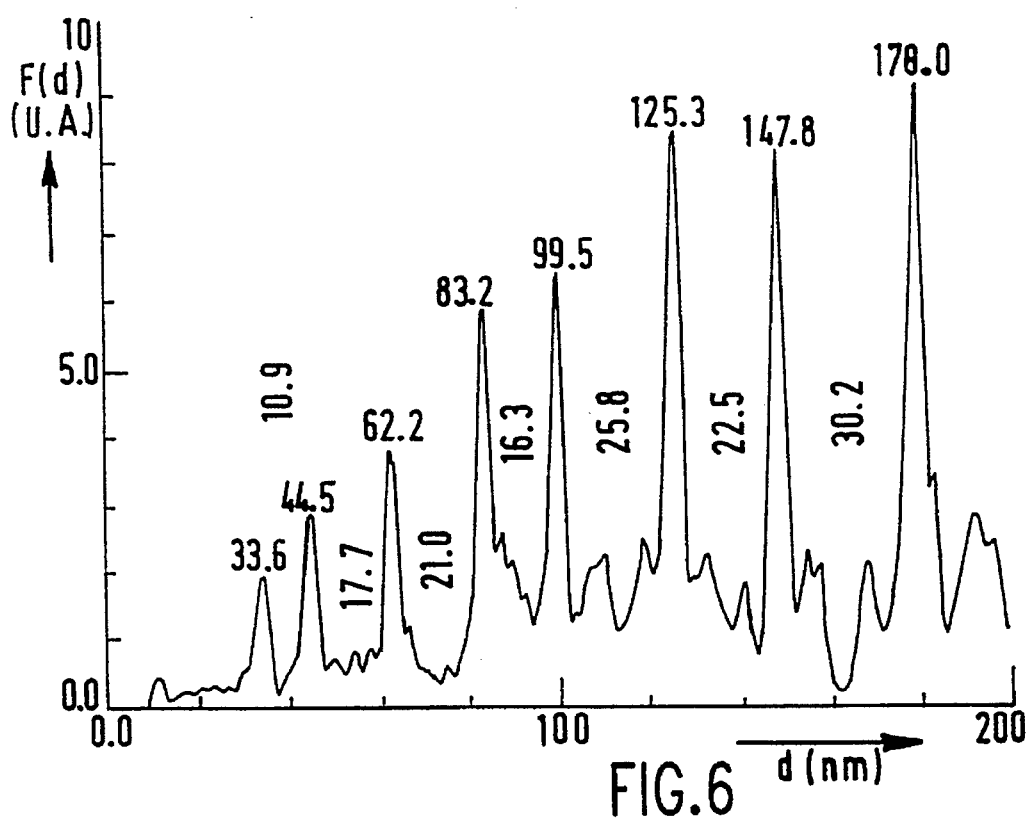
FIG. 6 shows the reflected intensity F(d) as a function of the distance d measured in the multi-layer structure of FIG. 1a, starting from its upper surface, said intensity being obtained by processing the intensity data of FIG. 1b by means of the device in accordance with the invention.

This problem is solved by a device which includes means for performing the Transformation of the function $f(\theta)$, producing the curve of FIG. 1b, into a function $F(d)$ of the intensity as a function of the depth d, producing the curve of FIG. 6.

On the basis of the few data known at the start, being:

the value of the intensity I reflected by the real structure as a function of $\theta$;

the approximate composition of the layer materials, and their number;

the mean refractive index of the structure;

the refractive index of the substrate;

a Transformation will be performed of the function representing the intensity I as a function $\theta$ into another function representing the intensity I as a function of the depth d within the structure. This transformation will be referred to hereinafter as "the Transformation" or "said Transformation".

The proposed Transformation enables determination of interface depths $d_1$, $d_2$, ... $d_n$ with a precision of 0.5 nm, even if:

the refractive indices of the various layers deviate little;

the layers have thicknesses which vary greatly, the layers are very thin, for example mono-atomic.

The reflected intensity curve of FIG. 1b has been formed by varying the glancing angle $\theta$ between 0° and 4°. Actually, in order to estimate the distances d in the material to be tested, being in the order of from 1 to a few hundreds of nm, the angle $\theta$ must be small for d and $\theta$ to satisfy Bragg's law.

$\theta$ small means that the glancing angle remains between $\theta_c$, being the critical angle near 0 where the reflected intensity I equals 1, and $\theta_M$ which is smaller than or approximately equal to 4°.

The angle $\theta_M$ is that for which it is assumed that sufficient information is collected to identify all interfaces of the structure.

In the example described hereinafter;
the wavelength of the X-ray source $\lambda_{RX}$=4.5 nm, and $\theta$ is measured between 0° and 2°.

The range $\theta_{min}$–$\theta_{max}$ on which the Transformation is performed will be defined later within the interval $\theta_c$–$\theta_M$.

The curve of FIG. 6 exhibits numerous peaks. Each peak or maximum characterizes an interface of the structure of FIG. 1a. The depth d in the structure 10a is plotted on the horizontal coordinate and the intensity I is plotted on the vertical coordinate in arbitrary units between 0 and b 1.

The position of each peak characterizes the depth of an interface in the structure 10a with respect to the surface 4.

The height of each peak is influenced by numerous factors. In principle, the height of the peaks depends essentially on the difference between the refractive indices of the materials to each side of the interface.

However, the height of the peaks is also influenced by:
the steepness of the interface;
the roughness of the interface;
the angular resolution of the measuring system:
one of the means of the device formed by a filtering system.

Nevertheless, the device in accordance with the invention enables a function to be obtained, as represented by the curve of FIG. 6, of the intensity as a function of d, (F(d)), which provides the depths d and the associated intensities in such a manner that the cited performance and precision are achieved.

The device enabling the Transformation of the signal shown in FIG. 1b in order to obtain that shown in FIG. 6 offers the advantage that is supplies this image I as a function of d directly in a single pass.

Another advantage resides in the fact that, during the detection of the interfaces by way of the position of the peaks at $d_1$, $d_2$, $d_3$ etc. on the curve of FIG. 6, the parasitic peaks appearing at the positions $2d_1$, $3d_1$, etc., $2d_2$, $3d_2$ etc., $2d_3$, $3d_3$, etc. are very narrow in comparison with the principal peaks appearing at $d_1$, $d_2$, $d_3$ ... Moreover, when two interfaces are detected at the depths $d_1$ and $d_2$, respectively, the parasitic peaks appearing at $d_1-d_2$ and at $d_1+d_2$ are also small relative to the principal peaks.

The device in accordance with the invention thus enables the contribution of the peaks corresponding to the multiples, to the sums and to the differences of the depths d to be minimized and, hence renders the curve of FIG. 6 suitable to achieve the objects of the invention.

It appears that when a structure such as that shown in FIG. 1a exhibits numerous interfaces, the overmodulation appearing on the reflectivity curve of FIG. 1b is produced by the sum of several periodic functions.

One could then contemplate the application of a simple Fourier integral so as to obtain large values of an integral for each value relative to each of the sines of the sum in order to obtain a curve as shown in FIG. 6.

A problem would arise immediately because the wavelength of the overmodulation shown on the curve of FIG. 1b is not constant. It varies substantially, and notably in the range of small values of the angle $\theta$.

Therefore, if a Fourier integral is to be used to obtain a curve having a well-defined peak, relative to a given sine, and if this wavelength variation were not taken into account, a very wide peak would be obtained which could not be used for the determination of the interface depth.

It has been found that the Fourier integral could be applied if a structure comprising several layers were to present few interfaces which are not very deep, be it that the result obtained would not be very exact.

However, as soon as the structure comprises layers with a large interface depth, or interfaces situated very close to one another, there is no chance whatsoever that these interfaces will be detected by application of a simple Fourier integral.

A structure whose analysis in respect of depth of interfaces appears to be difficult is, for example that of a pseudo-morphic high electron mobility transistor (HEMT) comprising three main interfaces, the last of which is situated very far from the interface between air and the first layer of semiconductor material.

It is the object of the invention to provide a device which is capable of dealing with such difficult cases. In order to take into account the fact that the function $f(\theta)$, corresponding to the signal of the intensity reflected as a function of the glancing angle $\theta$, exhibits overmodulation which is the approximative sum of periodic functions with periods which vary monotonously as a function of the glancing angle $\theta$, in accordance with the invention the means for the Transformation of the measured function $f(\theta)$ of the intensity signal as a function of the glancing angle $\theta$, into the function $F(d)$ of the intensity signal as a function of the depth d within the structure, comprise means for integrating, in the domain $\theta_{min}$–$\theta_{max}$, the measured function $f(\theta)$ multiplied by a periodic function $K_i(d, \theta)$ of the depth d and the angle $\theta$ whose period varies as a function of the angle $\theta$ in the same monotonous fashion as that of the periodic functions constituting the components of the measured function $f(\theta)$.

Specifically, the periodic function $K_i(d, \theta)$ with a monotonously varying period may be a pseudo-sinusoidal function whose wavelength $\lambda$ varies monotonously as a function of $\theta$ in a given interval $\theta_{min}$–$\theta_{max}$.

The device in accordance with the invention comprises means for synthesizing such a periodic function $K_i(d, \theta)$ of the depth d and the angle $\theta$ whose period varies monotonously as a function of $\theta$.

Figure 2A:
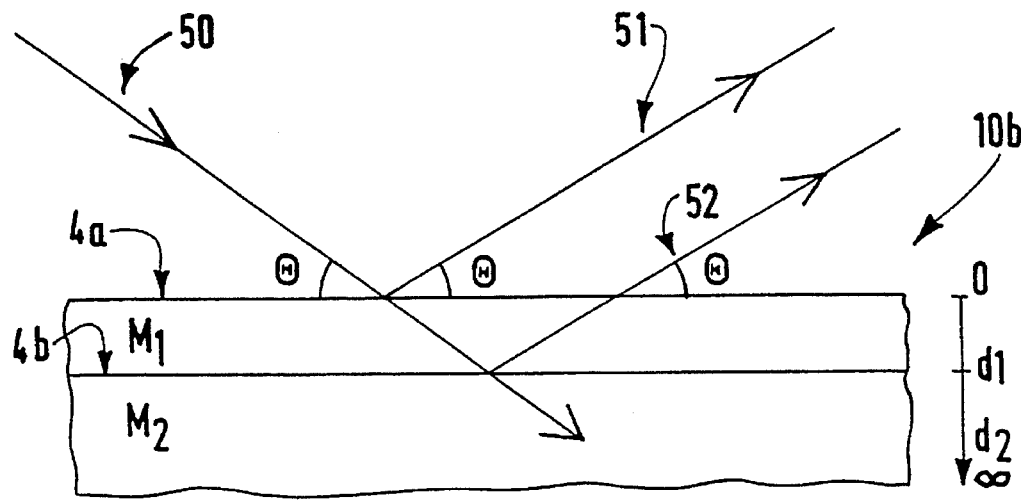
FIG. 2a shows a theoretical one-layer structure on a substrate.

FIG. 2a shows diagrammatically a theoretical structure 10b composed on the basis of known approximative data only relating to the real structure 10a.

The theoretical structure of FIG. 2a comprises two layers:

a lower layer $M_2$ having a thickness such that $d_2 = \infty$ in order to symbolize the thickness of a substrate, and the refractive index $n_2$ which is equal to the index of the substrate 100 of the real structure 10a to be tested;

an upper layer $M_1$ of an arbitrarily chosen thickness so that $d_1$ = from 100 to 200 nm, and a refractive index $n_1$ equal to the mean or approximative refractive index of the real structure 10a.

In this theoretical model incident rays 50 are considered to be reflected on the one hand by the upper surface 4a at 51 and on the other hand by the interface 4b of the layers $M_1/M_2$ at 52.

For the example described hereinafter, the following choice has been made:

for $M_1$, $d_1 = 100$ nm and real part of $(1 - n_1) = 13$ ppm;
for $M_2$, $d_2 = \infty$ and real part of $(1 - n_2) = 14.5$ ppm.

Figure 3A:
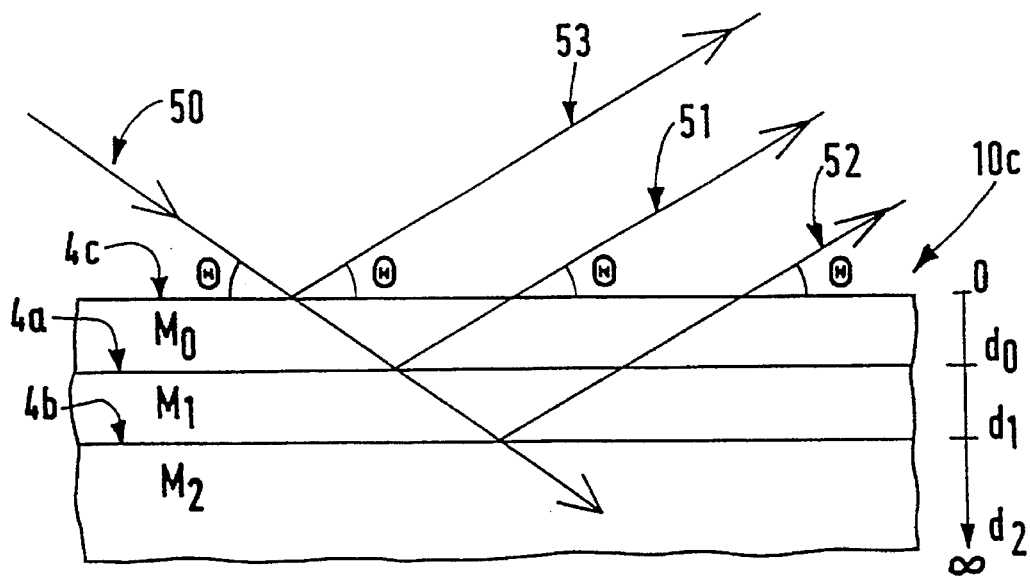
FIG. 3a shows a theoretical one-layer structure on a substrate, also provided with an upper oxide layer.

In the course of experiments performed by means of the device in accordance with the invention, it has been found that the use of the theoretical model 10b of FIG. 2a offers suitable results, but also that these results could be further improved by using another theoretical model 10c as shown in FIG. 3a.

The theoretical model 10c, being the preferred model, comprises three layers and is also composed on the basis of approximative data relating to the real structure 10a.

These layers are:

a lower layer $M_2$ having a thickness such that $d_2 = \infty$ in order to symbolize the substrate, and a refractive index $n_2$ equal to the index of the substrate 100 of the real structure 10a;

an intermediate layer $M_1$ having an arbitrarily chosen thickness so that $d_1$ = from 100 to 200 nm, and a refractive index $n_1$ in the order of magnitude of the mean index of the structure 10a;

an upper layer $M_0$ of oxide, having an arbitrarily chosen thickness so that $d_0 \approx 1$ nm, and a refractive index $n_0$ which deviates slightly from that of the layer $M_1$ situated therebelow.

In the theoretical model 10c, incident rays 50 are considered to be reflected at a glancing angle $\theta$ according to 53 by the upper surface 4c of the structure 10c, according to 51 by the interface 4a of the layers $M_0/M_1$, and according to 52 by the interface 4b of the layers $M_1/M_2$.

In this theoretical model 10c, principal reflection is to be understood to mean the reflection which is the sum of the reflection from the surface of the oxide layer $M_0$ and the reflection from the interface between the oxide and the first layer $M_1$. Actually, these two surfaces have substantially identical reflection coefficients.

In the example to be described hereinafter, the following choice has been made:

for $M_0$, $d_0 = 1$ nm real part of $(1 - n_0) = 9$ ppm;
for $M_1$, $d_1 = 100$ nm and real part of $(1 - n_1) = 13$ ppm;
for $M_2$, $d_2 = \infty$ and real part of $(1 - n_2) = 14.5$ ppm.

Using the device in accordance with the invention, a theoretical calculation of the reflectivity as a function of $\theta$ is then performed for one of the structures 10b or 10c, essentially consisting of:

a substrate of given index, on which there is provided a layer of given thickness and a refractive index very close to that of the substrate.

This theoretical calculation can be performed by way of simple means which are known to those skilled in the art, for example means programmed with the function providing the reflectivity. The results are subsequently stored in storage means 140.

Figure 2B:
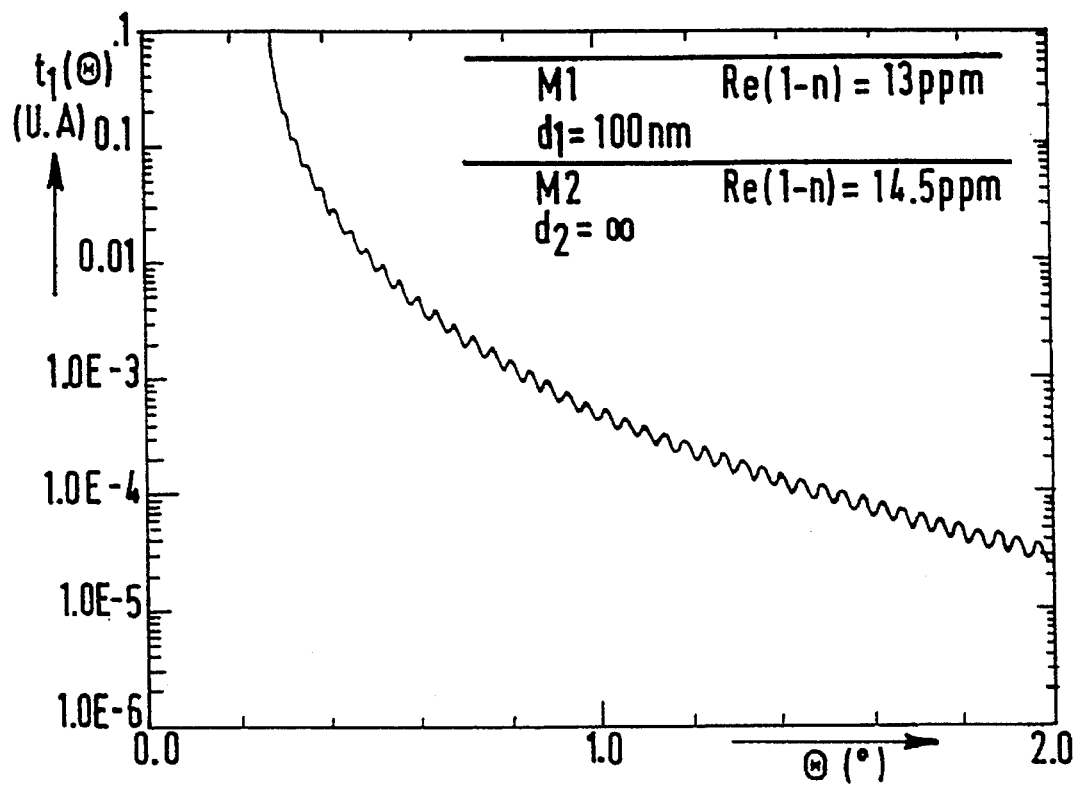
FIG. 2b shows the intensity $t_1(\theta)$ reflected by the theoretical structure of FIG. 2a, calculated as a function of the glancing angle $\theta$.
Figure 3B:
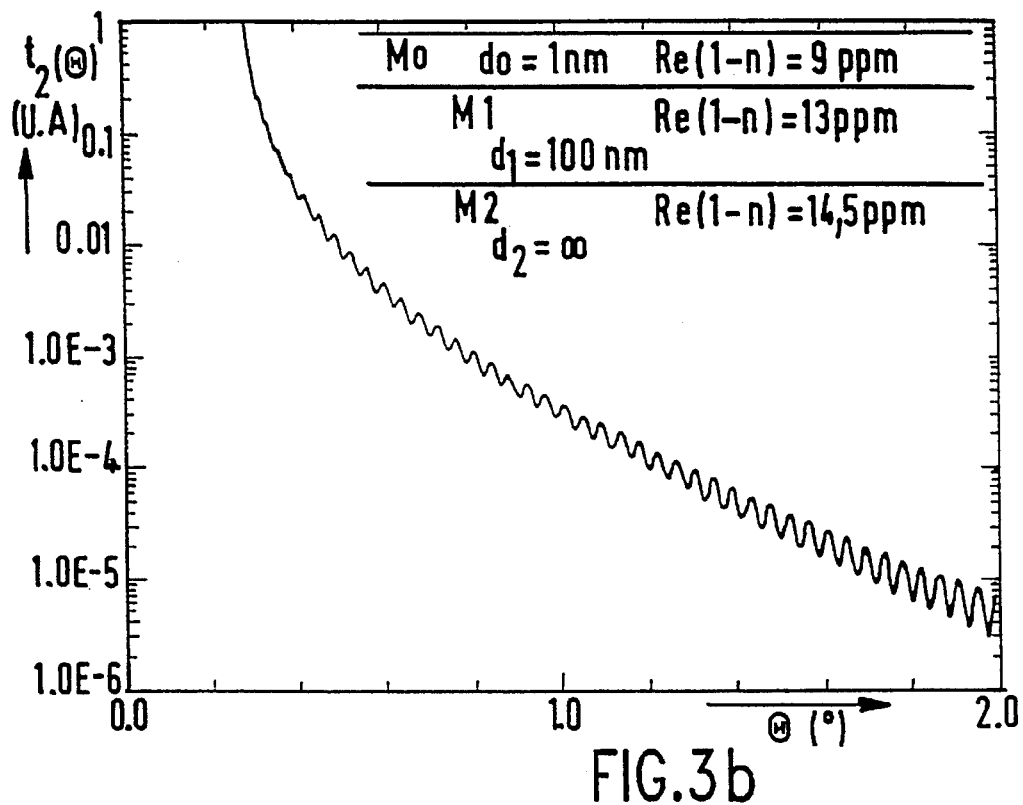
FIG. 3b shows the intensity $t_2(\theta)$ reflected by the theoretical structure of FIG. 3a, calculated as a function of the glancing angle θ.

For the structures 10b and 10c this results in the curves $t_1(\theta)$ and $t_2(\theta)$ of the FIGS. 2b and 3b. These curves represent the theoretical reflectivity which decreases as from $\theta_c$, being the critical angle, when the value of $\theta$ increases. Referring again to what has been said with reference to FIG. 1b, the curves of the FIGS. 2b and 3b exhibit an overmodulation.

In an alternative version of the device the theoretical calculation of the intensity I as a function of $\theta$ can be replaced by the theoretical calculation of Log I as a function of $\theta$.

In order to make the information relating to the overmodulation of the curves of the FIGS. 1b and 2b or 3b usable, in accordance with the invention, the function $f(\theta)$ producing the reflectivity measured as a function of $\theta$ is applied, as well as the functions $t_1(\theta)$ and $t_2(\theta)$ of the theoretical reflectivities, to a mathematical filter $F_1$. The falter $F_1$ is a bandpass falter of the high-pass type which transmits short wavelengths but not long wavelengths of the reflectivity curve.

The success of said means depends mainly on the characteristics of the filter $F_1$. This filter should not shift the signal in respect of $\theta$ and the rejection wavelength should be carefully chosen.

Figure 1C:
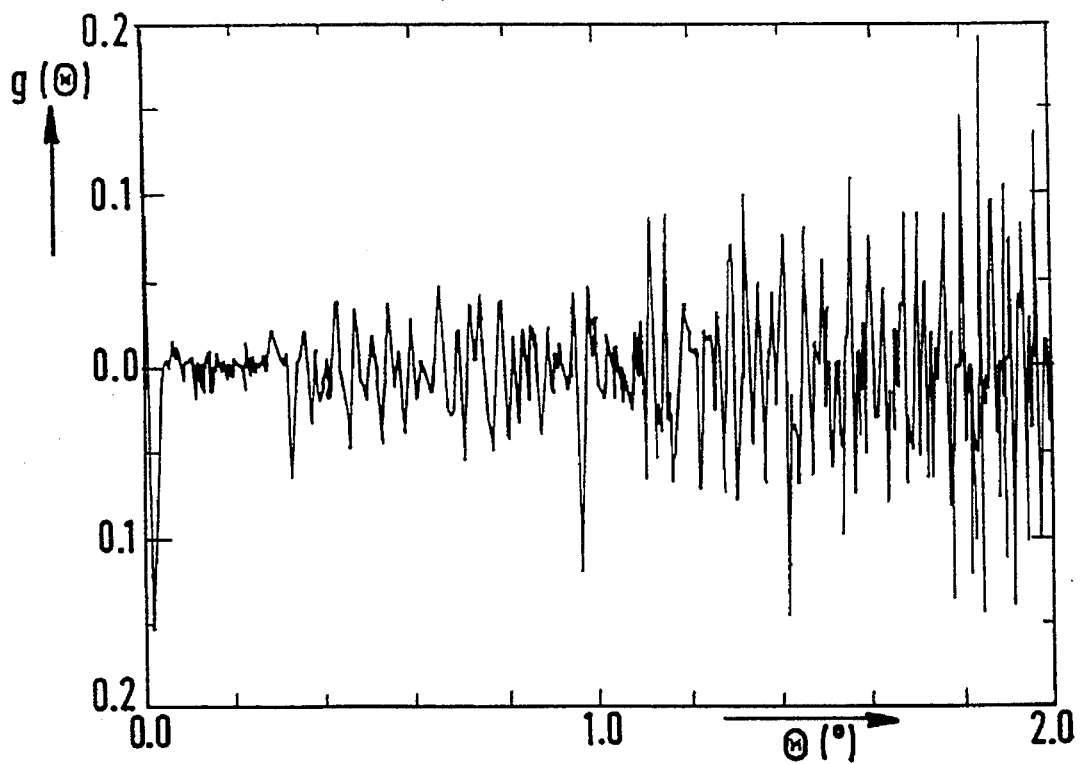
FIG. 1c shows the function $g(\theta)$ obtained by mathematical filtering of the function $f(\theta)$ shown in FIG. 1b.

After the filtering of the function $f(\theta)$ of the values measured in relation to the test structure 10a, there is obtained the function $g(\theta)$ shown in FIG. 1c which shows only the overmodulation.

Consequently, as before, the signal represented by the function $g(\theta)$ in FIG. 1c is a signal composed of different base signals having different frequencies (or wave-lengths $\lambda(\theta)$), expressed in the form of a sine sum, because each signal originates from the interference between the signal corresponding to the principal reflection from the upper surface of the structure and the signal corresponding to the reflection from an interface within the structure.

Figure 2C:
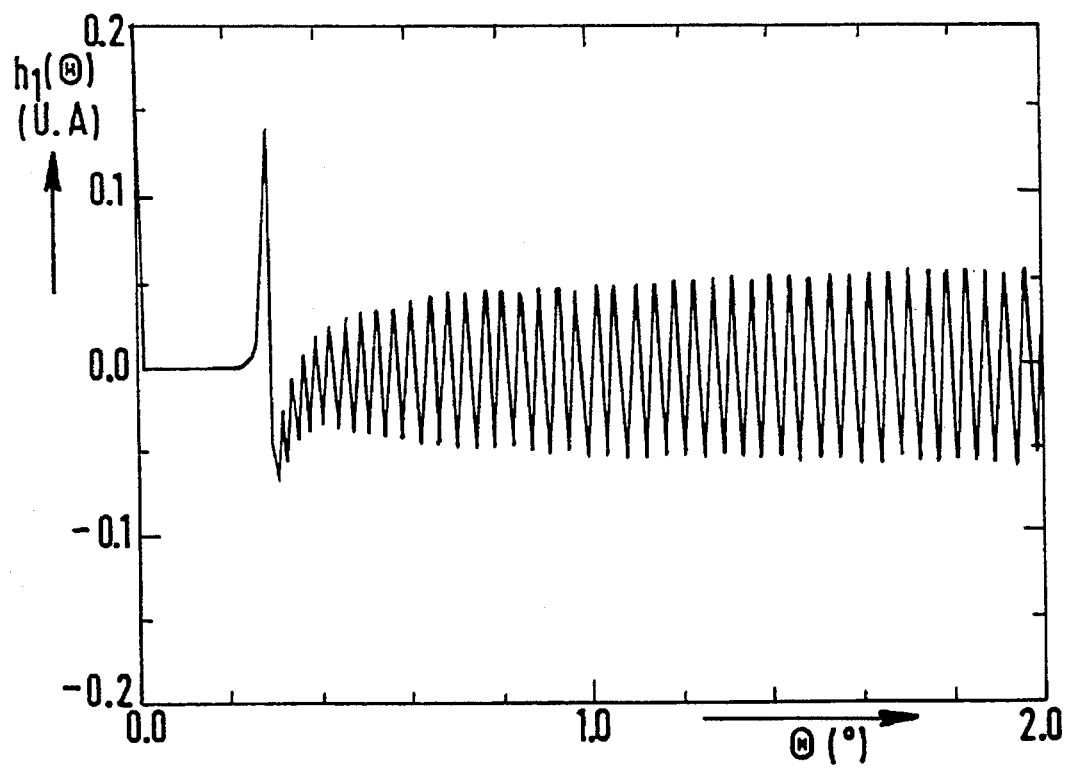
FIG. 2c represents the function $h_1(\theta)$ obtained after filtering of the function $t_1(\theta)$ of FIG. 2b by means of a filter which is identical to that used for obtaining the curve of FIG. 1c.
Figure 3C:
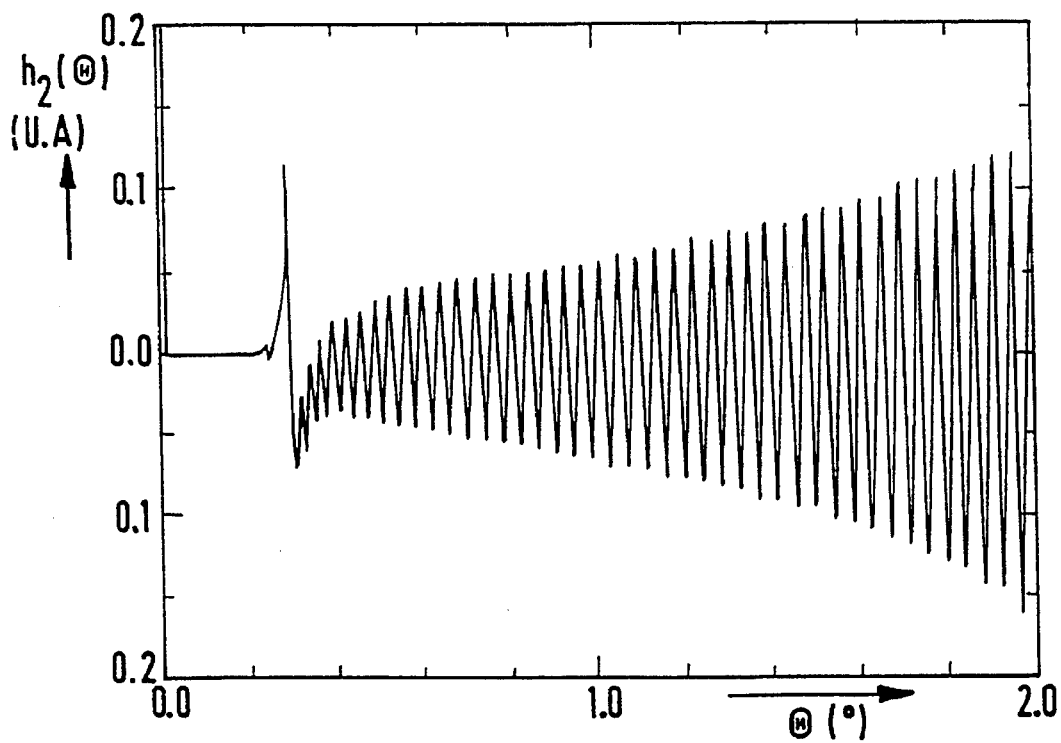
FIG. 3c shows the function $h_2(\theta)$ obtained after filtering of the function $t_2(\theta)$ of FIG. 3b by means of a filter which is identical to that used for obtaining the curve of FIG. 1c.

After the filtering of the theoretical functions $t_1(\theta)$ or $t_2(\theta)$ there are obtained the theoretical functions $h_1(\theta)$ or $h_2(\theta)$ which are shown in the FIGS. 2c and 3c, respectively, and which show only the overmodulation.

The appearance of the curve 1c, corresponding to the real structure, is quasi-periodic, whereas the appearance of the theoretical curves $h_1(\theta)$, $h_2(\theta)$ of the FIGS. 2c and 3c is that of a quasi-sinusoidal function whose wavelength $\lambda(\theta)$ varies as a function of $\theta$. In all case these theoretical curves show zero crossings. Thus, it is possible to define (or calculate) this wavelength $\lambda(\theta)$ by calculating the distances between the zeros.

An important discovery has been made in respect of this function $\lambda(\theta)$: it absolutely does not depend on the value of the depth d. Therefore, it is identical for all interfaces, regardless of the distance d between the interface and the upper surface of the structure considered. The variation of $\lambda(\theta)$ at least is identical for the systems of semiconductor materials.

Therefore, it suffices to know the approximate parameters of the materials of the structure to be studied, for example an approximate value of its refractive index relative to air, in order to enable determination of the variation of the wavelength $\lambda(\theta)$ of the filtered quasi-sinusoidal reflectivity curve $h_1(\theta)$ or $h_2(\theta)$ obtained on the basis of a theoretical structure, such as that of the FIGS. 2a or 3a, constructed by means of this approximate value.

Therefore, the Transformation in accordance with the invention aims to produce a theoretical quasi-periodic signal $k_i(d, \theta)$ having a period which depends on the angle $\theta$ in the same way as the measured signal.

The Transformation subsequently aims to multiply the experimental (or measured) signal $g(\theta)$ by the quasi-periodic theoretical signal $k_i(d, \theta)$ formed, followed by taking the integral of this result over all ranges of the angle $\theta$.

It appears that, knowing this variation of the wavelength $\lambda(\theta)$ of the theoretical reflectivity function, such a Transformation can be defined which can be applied to the real function $g(\theta)$ so as to obtain ultimately a curve representing the reflected intensity exclusively as a function of the depth of the interface d. Therefore, the theoretical structure has been built, and the theoretical reflected intensity curve $t_1(\theta)$ or $t_2(\theta)$ of the FIGS. 2a, 2b, 2c, or 3a, 3b, 3c has been formed, exclusively to enable the variation of the wavelength $\lambda(\theta)$ of the quasi-sinusoidal curve to be obtained.

As soon as the variation of the wavelength $\lambda(\theta)$ of the quasi-sinusoidal curve 2c or 3c is known, the measured curve of FIG. 1c, including a sine sum, can be integrated, taking into account the fact that each of the sines varies in respect of wavelength in the same way as the theoretical curve.

Therefore, after the filtering operation whose result $h_1(\theta)$ or $h_2(\theta)$ is shown in FIG. 2c or 3c, depending on the model chosen for the theoretical structure, $\lambda(\theta)$ is formed, followed by synthesising, on the basis of $\lambda(\theta)$, of said quasi-periodic signal $k_i(d, \theta)$ whose period depends on the function $\theta$ in the same way as that of each sine in the measured signal.

This function $\lambda(\theta)$ increases as from $\theta_c$ and tends towards a maximum $\lambda_{max}(\theta)$ for a glancing angle $\theta_{max}$. The angle $\theta_{max}$ taken into account will in principle be the maximum angle used during a test measurement performed on the real structure 10a.

Subsequently, preferably but not necessarily a relative wavelength $\lambda_{rel}(\theta)$ is defined by the ratio of $\lambda(\theta)$ to $\lambda_{max}(\theta)$, in order to normalize said wavelength $\lambda(\theta)$:

$$\lambda_{rel}(\theta) = \lambda(\theta)/\lambda_{max}(\theta).$$

Figure 3D:
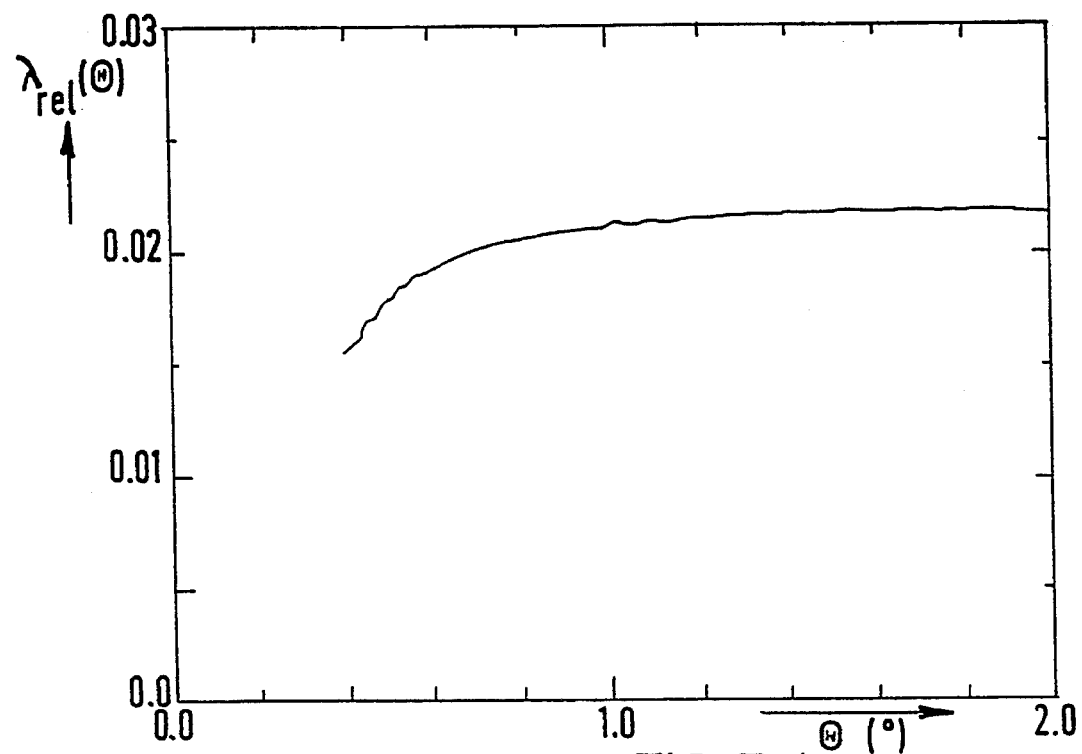
FIG. 3d shows the variation of the wave-length $\lambda(\theta)$ calculated on the basis of the filtered function of FIG. 3c.

The function $\lambda_{rel}(\theta)$ is shown in FIG. 3d. It has the same appearance as the function $\lambda(\theta)$.

Actually, it could be satisfactory to apply the later operations to the function $\lambda(\theta)$ itself. However, practical experiments for carrying out the invention have offered better results by applying these operations to $\lambda_{rel}(\theta)$, which thus represents an optimization of the method for using the device in accordance with the invention.

The function $\lambda_{rel}(\theta)$ no longer depends on the value of the depth d. Therefore, it is identical for all interfaces, regardless of the distance between the interface and the upper surface of the structure considered.

On the basis of the function $\lambda(\theta)$, or to be more exact $\lambda_{rel}(\theta)$, a new function will be the defined which will be referred to as CHIRP (and which will be written as CH). Using the function CHIRP, said quasi-sinusoidal function with a monotonous variation of the period $k_i(d, \theta)$ will be formed, that is to say a period which varies monotonously as a function of the wavelength $\lambda(\theta)$. A "monotonous" variation is to be understood to mean that it "always has the same sign".

Figure 3E:
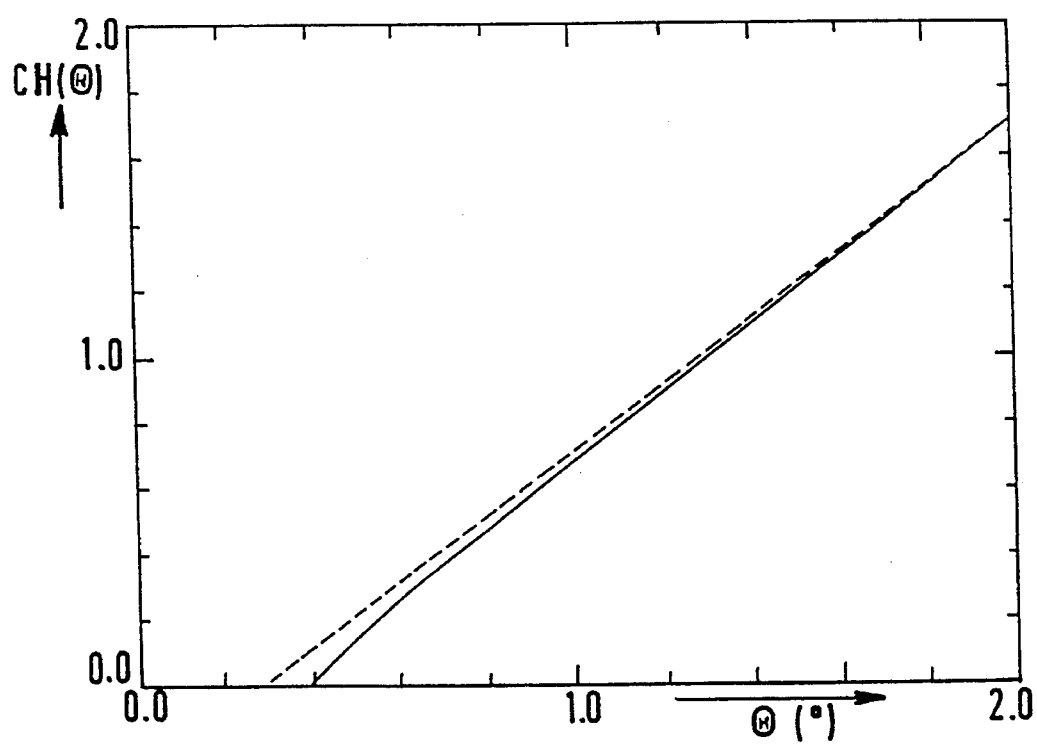
FIG. 3e shows the function CHIRP(θ)

The function CHIRP is written as:

$$CH(\theta_k) = CH(\theta_{k-1}) + 1/\lambda_{rel}(\theta_k)$$

and is shown in FIG. 3e. It appears that it is an increasing function.

The curve $\lambda(\theta)$ has been determined in a discrete manner by way of a series of points applied to FIG. 3d for each glancing angle $\theta_1, \theta_2, \ldots \theta_{k-1}, \theta_k$ with which the theoretical intensity calculation is made. Therefore, the function CH is also calculated in a discrete manner. The proposed formula enables a change-over from the series of points of the curve of FIG. 3d to the series of points of the curve of FIG. 3e which represents the function $CH(\theta)$ obtained as a function of $\theta$.

In order to reach this step of the use of the device in accordance with the invention, thus far only the mean refractive index of the real structure to be tested has been required to construct a theoretical structure 10b or 10c. Using this single data, the function $CH(\theta)$ has been calculated.

The pseudo-sinusoidal function $k_i(d, \theta)$ searched is then formulated by means of the relation:

$$K_i(d,\theta) = \sin\left(\beta \cdot d \cdot CH(\theta) + i\frac{\pi}{2}\right)$$

where $\beta$ is a constant and i is equal to 0 or 1.

In comparison with the conventional Fourier integral, the function $\sin\theta$ has now been replaced by a function $\sin(d, \theta)$ whose wavelength varies as described above. The drawbacks that would occur when use is made of a simple Fourier integral are thus eliminated.

In order to ensure that the final result is not excessively influenced by a shift of the angle of the measured signal, the device in accordance with the invention performs two operations during the integration:

a first multiplication of $g(\theta)$ by the quasi-sinusoidal theoretical signal formed, followed by a second multiplication by an identical signal which has the same quasi-period but has been shifted ¼ period.

The transformation thus comprises a first integral with the non-shifted signal formed and a second integral with the shifted signal formed, followed by the summing of the absolute value of these integrals.

This result is obtained by applying the quasi-sinusoidal theoretical signal in the form of a sine in the first integral, and subsequently in the form of a cosine in the second integral, resulting in the desired shift by ¼ period.

If a restriction to the calculation of a single integral were made for the transformation, the case could be encountered where the result would be zero because of the shifting of the measured signal.

Therefore, the signal $g(\theta)$ shown in FIG. 1c and obtained at the end of the filtering operation, performed by the mathematical filter $F_1$, of the function $f(\theta)$ shown in FIG. 1b, is considered and the following two integrals are applied thereto:

$$G(d) = \left| \int_{\theta_{min}}^{\theta_{max}} g(\theta) \cdot K_o(\theta,\lambda) d\theta \right| + \left| \int_{\theta_{min}}^{\theta_{max}} g(\theta) \cdot K_1(\theta,\lambda) d\theta \right|$$

A further improvement is obtained by performing a new operation, producing a function G'(d) which is the function G(d) divided by the interval $\theta_{min}$, $\theta_{max}$ so that: G'(d)=G(d)/($\theta_{max}-\theta_{min}$). The functions $K_1$ and $K_2$ are given by:

$K_o = \sin(\beta.d. CH(\theta))$ $K_1 = \cos(\beta.d. CH(\theta))$ in which $\beta$ is a constant equal to $4\pi/\lambda_{RX}$ and d is the depth within the real structure. (It is to be noted that $\lambda_{RX}$ is the wavelength of the X-ray source).

Thus, the absolute value of each of the integrals is taken and the sum of these absolute values is formed.

In these integrals not only the filtered experimental function $g(\theta)$ can be recognized, but also the two functions, one of which implements the sine of the synthesized pseudo-sinusoidal function described above, whereas the other implements a cosine of the same parameters and variables.

In order to ensure that the integral in accordance with the invention offers suitable results, the integral interval must be correctly chosen: integration is required over an integer number of periods of the selected theoretical function $h_1(\theta)$ or $h_2(\theta)$. It is also necessary to integrate over an integer number of periods which is as large as possible within the range $\theta_c-\theta_M$ considered. Therefore, on the curve of FIG. 2c, or that of FIG. 3c, first of all a minimum angle and a maximum angle are chosen, which angles define the range within which the Transformation is to be performed. Subsequently, the entire interval for the integration is defined: $\theta_{min}-\theta_{max}$. The angle $\theta_{min}$ is defined as the first zero of the curve of FIG. 2c or 3c found when $\theta$ increases. The sign of the derivative of the function $h_1$ or $h_2$ at this first zero is therefore considered, after one proceeds towards the end of the interval chosen, that is to say towards the maximum angle chosen; on the basis of the latter, one descends again to the first zero where the function $h_1$ or $h_2$ presents a derivative of the same sign. The largest possible integration interval $\theta_{min}-\theta_{max}$ with an integer number of periods of the function $h_1$ or $h_2$ has thus been defined. Evidently, the angles $\theta_{min}$ and $\theta_{max}$ depend on the variable d and, very strictly speaking, should be written as $\theta_{min}(d)$ and $\theta_{max}(d)$. Hereinafter, however, $\theta_{min}$ and $\theta_{max}$ are written for the sake of simplicity.

The angle $\theta_{min}$ is chosen to be close, but not too close, to the critical angle $\theta_c$ in order to avoid any distortions. For the practical analysis of the structures of semiconductor materials $\theta_{min}$ is chosen in the order of magnitude of 0.4° C. The angle $\theta_{max}$ is chosen to be as remote therefrom as possible, still avoiding the range in which the noise becomes too excessive. Actually, when the curve $f(\theta)$ of FIG. 1b is considered, it appears that the noise becomes strong for the high values of $\theta$ because the measured intensity becomes low. Therefore, it is often necessary to terminate the integration interval before reaching the maximum angle $\theta_M$ used to perform the measurement $I=f(\theta)$.

However, it is necessary to take into account the fact that the larger the range of $\theta$ is chosen, that is to say the interval $\theta_{min}-\theta_{max}$, the finer the peaks of the curve $I=f(d)$ of FIG. 6 will be and also the better the definition of the interface depths $d_1, d_2, \ldots d_n$ will be.

Figure 5:
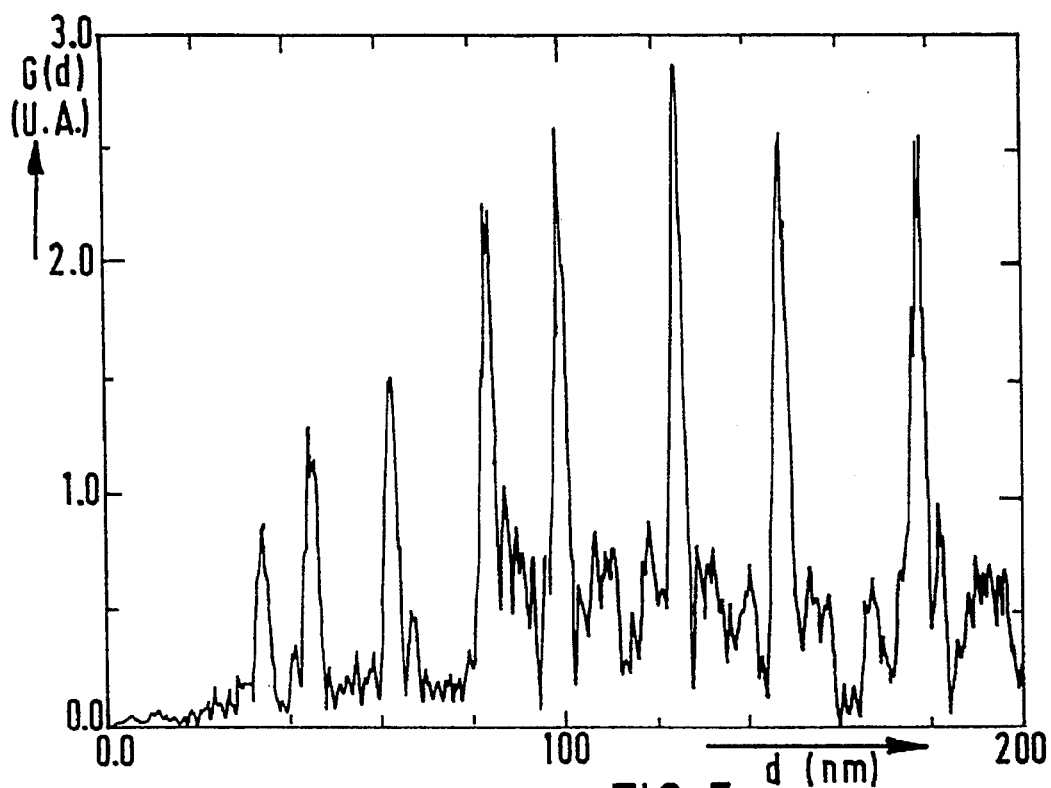
FIG. 5 shows diagrammatically the function of the integration result G(d) without smoothing.

The result of the Transformation is not yet the function G(d) itself, as given above. Actually, this function G(d) is very uneven as shown in FIG. 5; it comprises numerous very fine and closely spaced peaks. If the result of the Transformation would be limited to the curve representative of the function G(d), it would be crowded with non-essential, useless information.

Therefore, the function G(d) as obtained after the integration is applied to a filter $F_2$ which realizes a symmetrical diffusion. The symmetrical diffusion provides smoothing of the fine and multiple peaks, without shifting the maximum value of the peak at $\theta$. The filter $F_2$ is a low-pass filter.

This produces the desired function F(d) shown in FIG. 6, in which the position of the peaks and their relative height provide a direct representation of the depths $d_1, d_2, d_n$ of the interfaces of the real structure 10a to be tested and the associated intensities. Consequently, the exact concentration x of the elements in the layers can be calculated.

Finally, the Transformation in accordance with the invention resembles a simple Fourier transform. However, it is not such a transform.

Specifically, the functions sin and cos of the conventional Fourier transform are considered between the limits $-\infty, +\infty$, so that we have periodic functions with a limited interval. On the other hand, the wavelength of these functions varies as the wavelength relating to a theoretical structure 10b or 10c, composed by means of a layer on a substrate, the refractive index of said layer deviating only slightly from that of the substrate. This means that the argument of the sines and cosines varies.

For the majority of applications of the invention, the function CHIRP can be calculated directly from $\theta$ by means of the following relation:

$CH(\theta) = (\sin^2\theta - \sin^2\theta_c)^{1/2}/\cos\theta$ and be used in this form in the integrals for calculating the function G(d).

This function can also be written for the small angles with the following approximation:

$CH(\theta) = (\sin^2\theta - \sin^2\theta_c)^{1/2}$

This direct means for evaluating the function $CH(\theta)$ has been obtained in accordance with the invention on the basis of the previously described more complex implementation, and hence constitutes an approximation of the function obtained point by point on the basis of $\lambda(\theta)$ shown in FIG. 3e.

However, this calculated function is very close to the previous one. The difference is actually minimum and negligibly small in the majority of cases.

In the above description the means for achieving the object of the invention by forming a quasi-sinusoidal function $h_1$ or $h_2$, followed by the formation of the function $CH(\theta)$ and the synthesis of the quasi-sinusoidal function $\sin(d, \theta)$ have been mentioned.

However, the quasi-sinusoidal functions $K_i(d,\theta)$ of the integral G(d) can very well be replaced by quasi-periodic functions whose period varies monotonously as a function of $\theta$ in the same way. For example, periodic triangular functions can be used.

In the foregoing the possibility of starting with a hypothetical structure 10c with an oxide layer has been presented: this hypothesis is particularly valid when the real structure 10a itself is covered with an oxide layer. This is very common practice in contemporary semiconductor devices.

Therefore, if the real structure comprises an oxide surface and if, the calculation utilizing the theoretical structure without oxide (FIG. 2a), or the direct mathematical formulation of CHIRP (θ) is used to achieve the object of the invention, the positions of the interfaces $d_1, d_2, \ldots d_n$ will be evaluated with a gap of at least 1 nm with respect to their exact position. These positions, however, will be better evaluated by adopting the calculation approach corresponding to the structure with oxide (FIG. 3a).

Nevertheless, so long as the oxide of the real structure is thin, a very good approximation is obtained by performing the direct calculation of CH(θ) and a considerable amount of calculation time is saved and the complexity of the device is less.

Therefore, in the majority of cases the direct calculation of CH(θ) will be performed, the means for a more exact calculation, if any, being maintained in the device.

Any shift between the results obtained with and without taking into account the oxide layer occurs for the following reasons.

When the upper surface of a layer structure is covered with an oxide, two interfaces occur near one another:

the first interface: air-oxide the second interface: oxide-semiconductor, which interfaces have a reflectivity of the same order of magnitude.

It has already been stated that in this case the oxide layer is considered as a mean interface. However, the position of this mean interface between said first and said second real interface depends on the effective thickness of the oxide. As the oxide is thicker, the error induced by adopting the mean interface will be greater.

The device in accordance with the invention can be used, as opposed to the devices which utilize the comparisons with Classification Tables, for structures in which the layers exhibit very small differences in respect of indices, except for the upper oxide layer. For index differences in excess of 1.5 ppm, the linearities are lost and, consequently, the direct representation of d becomes less exact.

The invention aims for a practical application for heterostructures of semiconductor materials exhibiting small index differences, for example:

GaAs, GaAlAs, GaInAs, AlInAs, InP, with numerous possible variations and combinations of ternary and quaternary combinations;

the systems Si—Ge,

Cd—Hg—Te,

Zn—S, Zn—Se, Zn—Cd, etc.

This method can also be applied for cladding layers on non-semiconductor substrates.

Referring to FIG. 4b, the device in accordance with the invention thus comprises the following functional blocks:

a functional block 130 for storing the measured data I=f(θ) relating to the real structure 10a to be tested;

a functional bloc 131 for plotting the curve representing I=f(θ) as shown in FIG. 1b.

The device also comprises the following functional blocks:

a block 140 for storing data concerning the real structure 10a, that is to say the refractive index of the substrate, the mean refractive index of the assembly of layers of the real structure, the wavelength $\lambda_{RX}$ of the incident X-rays;

a block 141 for defining a hypothetical structure 10b or 10c on the basis of the data from the preceding block 140;

a block 142 for calculating the reflectivity

I=$t_1$(θ) or I=$t_2$(θ) relating to one of the hypothetical structures 10b or 10c chosen.

The output of the block 142 is applied to the block 131 for plotting the representative curve so as to obtain the curves $t_1(\theta)$ and $t_2(\theta)$ as shown in the FIGS. 2b and 2c.

The output of the curve plotting block 13 1 is applied to a functional block 132 in which the filter $F_1$ filters all functions at this stage, that is to say the measured function f(θ) for obtaining the function g(θ) as well as the theoretical function $t_1(\theta)$ for obtaining the function $h_1(\theta)$ or the theoretical function $t_2(\theta)$ for obtaining the function $h_2(\theta)$.

The theoretical functions $h_1(\theta)$ or $h_2(\theta)$ are subsequently applied to the functional block 143 which performs the calculation of λ(θ), and possibly of $\lambda_{rel}(\theta)$, and subsequently in the block 144 CH(θ) is calculated on the basis of λ(θ) or $\lambda_{rel}(\theta)$.

The function g(θ) supplied by the filter block 132 and the function CH(θ) supplied by the block 144 are subsequently introduced into a block 134 for calculating integrals so as to supply the function G(d).

Subsequently, the function G(d) is applied to the diffusion filter $F_2$ in the form of the block 135. The output of the block 135 thus supplies the result function F(d) of the Transformation in accordance with the invention.

Finally, the ultimate function F(d) is applied to the plotting block 137 which supplies the representative curve shown in FIG. 6.

Between the filter block 135 and the block 137 there is provided a block 136 which performs the calculations relating to the exact position of the interfaces and to the interpolation of the intensities associated with the peaks in order to determine the composition of the layers to both sides of each interface.

In comparison with FIG. 4a, the device has been simplified. It does not include the calculation of λ(θ) but exclusively the direct calculation of $$CH(\theta)=(\sin^2\theta-\sin^2\theta_c)^{1/2}/\cos(\theta)$$

in a block 144'. The other blocks have the same functions as those of FIG. 4b.

I claim:

1. A device for processing a measured signal corresponding to an intensity reflected, as a function of an glancing angle (θ) at an X-ray wavelength ($\lambda_{RX}$), by a real multi-layer structure stacked on a substrate (100), which layers exhibit small differences as regards refractive index at their interfaces, which processing device comprises means for transforming the function (f(θ)), corresponding to the reflected intensity signal measured as a function of the glancing angle (θ) in a range of glancing angles which is bounded by minimum and maximum angular values $\theta_{min}$, $\theta_{max}$, into a function (F(d)) corresponding to the intensity signal formulated as a function of the depth (d) within the real multilayer structure, said function (F(d)) obtained enabling a direct representation to be formed of the depth of each interface ($d_1, d_2, \ldots d_n$) of the real structure, and of the associated reflected intensities.

2. A device as claimed in claim 1, wherein function (f(θ)) corresponding to the intensity signal reflected as a function of the glancing angle (θ) presenting an overmodulation which is approximately the sum of periodic functions with periods varying monotonously as a function of the glancing angle (θ), the means for transforming the measured function (f(θ)) of the intensity signal as a function of the glancing angle (θ) into the function (F(d)) of the intensity signal as a function of the depth (d) within the structure comprise means for integrating, over the range $\theta_{min}$–$\theta_{max}$, the measured function (f(θ)) multiplied by a periodic function $k_i$(d, θ) of the depth (d) and of the glancing angle (θ) whose period varies monotonously as a function of the glancing angle (θ) in the same way as that of the periodic functions which are the components of the measured function (f(θ)).

3. A device as claimed in claim 2, further comprising a first filter $F_1$ of the high-pass type which serves to cut-off the long wavelengths of the measured reflected intensity signal $f(\theta)$.

4. A device as claimed in claim 3, further comprising means for synthesizing said periodic function $k_i(d,\theta)$ of the depth (d) and the glancing angle ($\theta$) whose period varies monotonously as a function of the angle ($\theta$) of incidence in the angular range $\theta_{min}-\theta_{max}$, which synthesizing means comprise at least calculation means applied to a hypothetical structure comprising at least one layer having a refractive index in the vicinity of the mean refractive index of the real multi-layer structure, said layer being provided on a substrate having a refractive index substantially equal to that of the real structure, and possibly an upper oxide layer, which calculation means include:

first means for calculating a function corresponding to a theoretical reflected intensity signal at the wavelength of X-rays ($\lambda_{RX}$) as a function of the glancing angle ($\theta$) in the range of glancing angles $\theta_{min}-\theta_{max}$, second means for calculating a function ($\lambda(\theta)$) corresponding to the wavelength calculated for each of the values $\theta_1, \theta_2, \theta_k \ldots$ of the glancing angle $\theta$ in the angular range $\theta_{min}-\theta_{max}$, third means for calculating a function (CH($\theta$)) exhibiting the same monotonous variation as a function of the angle ($\theta$) as that of the components of the function measured, said function CH($\theta$) being formulated by the relation $CH(\theta_K) = CH(\theta_{K-1}) + 1/\lambda(\theta)$, said periodic function $k_i(d, \theta)$ being formulated by $\sin(\beta.d. \text{ CH } \theta)) + i \pi/2)$, where i=0 or 1 and $\beta$=constant.

5. A device as claimed in claim 4, further comprising a filter $F_1$ of the low-pass type for cutting off the long wavelengths of the theoretical reflected intensity signal.

6. A device as claimed in claim 5, wherein the integration means perform the calculation of integrals and form the sum of their absolute value in accordance with the relation:

$$G(d) = \left| \int_{\theta_{min}}^{\theta_{max}} f(\theta) \cdot k_0(d,\theta) \cdot d\theta \right| + \left| \int_{\theta_{min}}^{\theta_{max}} f(\theta) \cdot k_1(d,\theta) \cdot d\theta \right|$$

7. A device as claimed in claim 6, further comprising a symmetrical diffusion filter $F_2$ so as to smooth the function G(d) resulting from the integration and to obtain the transformation function F(d).

8. A device as claimed in claim 6, wherein the integration means perform the calculation of the integrals and form the sum of the absolute value in accordance with the relation:

$$G'(d)=G(d)/(\theta_{max}-\theta_{min})$$

9. A device as claimed in claim 8, further comprising a symmetrical diffusion filter $F_2$ so as to smooth the function G(d) resulting from the integration and to obtain the transformation function F(d).

10. A device as claimed in claim 3, further comprising means for synthesizing said periodic function of the depth (d) and the glancing angle ($\theta$), formulated by sin (d, $\theta$) whose period varies monotonously as a function of the glancing angle ($\theta$) in the range $\theta_{min}-\theta_{max}$, which synthesizing means comprise at least means for calculating a function (CH($\theta$)) presenting the same monotonous variation as a function of the angle ($\theta$) as that of the components of the measured function, which function CH is formulated by the relation:

$$CH(\theta)=(\sin^2\theta-\sin^2\theta_c)^{1/2}/\cos\theta$$

where $\theta_c$=the value of the critical angle for the real multilayer structure formed at the operating wavelength $\lambda_{RX}$ of X-rays, said periodic function being formulated by T,240 where $\beta$ is a constant equal to $4\pi/\lambda_{RX}$ and where i is equal to 0 or 1.

11. A device as claimed in claim 10, wherein the integration means perform the calculation of integrals and form the sum of their absolute value in accordance with the relation: T,270

12. A device as claimed in claim 11, further comprising a symmetrical diffusion filter $F_2$ so as to smooth the function G(d) resulting from the integration and to obtain the transformation function F(d).

13. A device as claimed in claim 11, wherein the integration means perform the calculation of the intergrals and form the sum of the absolute value in accordance with the relation:

$$G'(d)=G(d)/(\theta_{max}-\theta 12_{min})$$

14. A device as claimed in claim 13, further comprising a symmetrical diffusion filter $F_2$ so as to smooth the function G(d) resulting from the integration and to obtain the transformation function F(d).

* * * * *